United States Patent

Minami et al.

[11] Patent Number: 6,150,549
[45] Date of Patent: Nov. 21, 2000

[54] SILANE COMPOUND

[75] Inventors: Masaki Minami; Keizo Ikai; Mitsuo Matsuno, all of Yokohama, Japan

[73] Assignee: Nippon Mitsubishi Oil Corporation, Tokyo, Japan

[21] Appl. No.: 09/126,254

[22] Filed: Jul. 30, 1998

[30] Foreign Application Priority Data

Jul. 31, 1997 [JP] Japan ..... 9-219020
Jul. 31, 1997 [JP] Japan ..... 9-219021

[51] Int. Cl.$^7$ ..... C07F 7/08
[52] U.S. Cl. ..... 556/465; 556/487
[58] Field of Search ..... 556/465, 487

[56] References Cited

U.S. PATENT DOCUMENTS

| | | | |
|---|---|---|---|
| 3,567,754 | 3/1971 | Alsgaard | 556/487 |
| 4,297,499 | 10/1981 | Koga et al. | 556/465 |
| 4,309,558 | 1/1982 | Koga et al. | 556/487 |
| 5,646,326 | 7/1997 | Schuler | 556/474 |
| 5,856,543 | 1/1999 | Friedrich et al. | 556/465 |
| 5,874,603 | 2/1999 | Arkles | 556/465 |

OTHER PUBLICATIONS

Akira Watanabe and Minoru Matsuda, "Electrical and Optical Properties of Heat–treated Silicon Network Polymers", Chemistry Letters, pp. 1101–1104, Jul. 1991.

*Primary Examiner*—Paul F. Shaver
*Attorney, Agent, or Firm*—Akin, Gump, Strauss, Hauer & Feld, L.L.P.

[57] ABSTRACT

A novel silane compound is disclosed, which is used as a suitable strating material (monomer) of polysilane eligible for the precursor of electroconductive- and photoconductive-materials such as phtoresists as well as polymerization initiators and silicone carbide-based ceramics and which is useful for chemical vapor deposition.

4 Claims, No Drawings

SILANE COMPOUND

BACKGROUND OF THE INVENTION

1. Field of the Invention

This invention relates to novel silane compounds, more particularly to a silane compound which is used as a starting material (monomer) of polysilane to be used as a precursor of electro-conductive- and photoconductve-materials, photo-reactive materials such as photoresists, polymerization initiators and silicone carbide-based ceramics and which is useful for chemical vapor deposition.

2. Description of the Related Art

In recent years, an attempt has been made on use of polysilanes as materials for the production of photoconductive materials. For instance, a material increased in electro-conductivity can be produced by doping a straight-chain-like polymethylphenylsilane with $AsF_5$.

Another attempt has been made on the production of electro-conductive or photoconductive materials by thermal decomposition of a polysilane in which instance according to the report made in Chem. Lett., 1101 published in 1991, polyphenylsilane having a molecular structure of networks is formed into a film and then thermally decomposed in a vacuum thereby obtaining an SiC film and furthermore the thermal decomposition at a temperature of 600° C. results in the formation of a serniconductive film having an Eg.opt value of 1.1 eV.

However, polyphenylsilane is unsuitable as a material for the production of a electro-conductive or photoconductive material because its hydrocarbon substituent is low in elimination properties in the thermal decomposition process, causing that the hydrocarbons remains in the resulting material obtained after the thermal decomposition. Moreover, since the thermal decomposition is necessarily conducted in a vacuum, the production cost of such a semiconductive film tends to be high.

SUMMARY OF THE INVENTION

A novel silane compound has now been found by the present inventors as a result of an extensive research with the foregoing drawbacks in view.

According to the present invention, there is provided a silane compound which is useful for the production of a polysilane and represented by the formula

  (I)

wherein X is a hydrogen atom or a halogen atom, Q is selected from a group represented by the formula

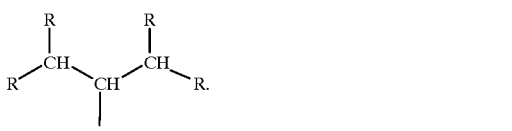  (II)

wherein R is a methyl or ethyl group and may be the same or different and a group represented by the formula

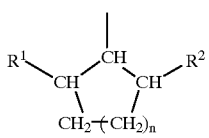  (III)

wherein $R^1$ is a hydrogen atom or a $C_1$–$C_4$ alkyl group, $R^2$ is a $C_1$–$C_4$ alkyl group and n is an integer of 1 or 2, provided that $R^1$ is not a hydrogen atom if $R^2$ is a methyl group and n is 2 or $R^2$ is a methyl group and X in formula (I) is a halogen atom.

DETAILED DESCRIPTION OF THE INVENTION

One of the inventive silane compounds is one represented by the formula

  (I)

wherein Q is a group represented by the formula

  (II)

This silane compound is hereinafter referred to as alkylsilane.

Therefore, the alkylsilane according to the invention is represented by the formula

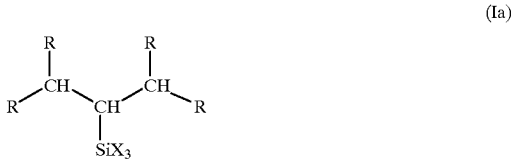  (Ia)

In formula (Ia), X is a hydrogen atom or a halogen atom such as fluorine, chlorine, bromine and iodine among which chlorine is particularly preferred.

In formula (Ia), the groups indicated by R each are a methyl or ethyl group and may be the same or different.

Specific examples of the inventive alkylsilane of formula (Ia) include 2,4-dimethyl-3-silylpentane, 2,4-dimethyl-3-silylhexane, 3,5-dimethyl-4-silylheptane, 3-ethyl-5-methyl-4-silylheptane, 3,5-diethyl-4-siiylheptane,2,4-dimethyl-3-trichlorosilylhexane, 3,5-dimethyl-4-trichlorosilylheptane, 3-ethyl -5-methyl -4-trichlorosilylheptane and 3,5-diethyl-4-trichlorosilylheptane.

No particular limitation is imposed on the method for producing the inventive alkylsilane. Therefore, there may be used a variety of synthesis methods and typical examples thereof are described as follows.

A first example of the method for synthesizing the alkylsilane represented by formula (Ia) wherein three halogen atoms are bonded to the silicone atom, that is, an alkyltrihalogenosilane is conducted by reacting an organic metal compound represented by the formula (a)

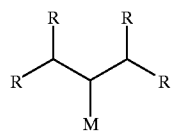

with a tetrahalogenated silicone as indicated by the formula

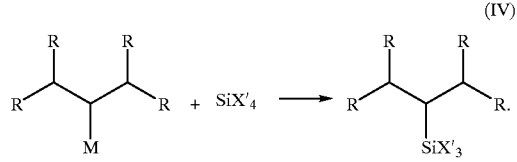
(IV)

In these formulae, each R is the same as those in formula (Ia), X' is a halogen atom and M is lithium or halogenated magnesium.

Eligible organic metal compounds of formula (a) are 2,4-dimethyl-3-lithopentane, 2,4-dimethyl-3-lithohexane, 3,5-dimethyl-4lithoheptane, 3-ethyl-5-methyl-4-lithoheptane and 3,5-diethyl-4-lithoheptane.

These organic metal compounds can be easily obtained by reacting halogenated alkan with lithium or magnesium in an etherial solvent such as diethylether and tetrahydrofuran.

A variety of tetrahalogenateds silane may be used for the reaction with the organic metal compound of formula (a). Particularly preferred is tetrachlorosilane.

Although there is no particular limitation to the method for conducting the reaction indicated by formula (IV), there is generally employed a method in which a solution of the organic metal compound of formula (a) in a polar solvent such as ether or tetrahydrofurane is subjected to a reaction with a solution of tetrahalogenated silane, typically tetrachlorosilane in a polar solvent such as ether or tetrahydrofurane. The reaction temperature is selective, depending on the kind of and the amount of the organic metal compound and is selected from the range of –20 to 100° C., preferably 0 to 80° C. The reaction time is selected from the range of 5 minutes to 10 hours, preferably 20 minutes to 5 hours.

Although the composition of charging the reaction materials is optional, the molar ratio of the organic metal compound of formula (a) to tetrahalogenated silane is desirably selected from the range of 0.5 to 1.2, preferably 0.8 to 1.1.

After completion of the reaction, the intended alkyltrihalogenosilane is obtained by filtrating the reaction mixture to remove the by-product salt and then distilling the filtrate.

A second example of the method for synthesizing the alkyltrihalogenosilane is conducted by reacting an olefin with trihalogenosilane in the presence of a radical initiator so as to hydrosilylating the olefin as indicated by the formula (V)

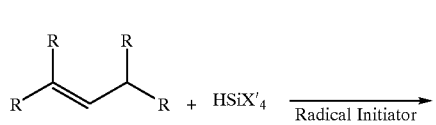

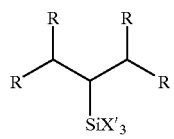

wherein each R is the same as those in formula (Ia) and X' is a halogen atom.

The olefins eligible for the reaction are 2,4dimethyl-2-penten, 2,4-dimethyl-2-hexene, 3,5-dimethyl-3-heptene, 3-ehtyl-5-methyl-3-heptene and 3,5-diethyl-3-heptene. A variety of trihalogenosilanes can be used among which trichlorosilane is particularly preferred.

Although not restricted, eligible radical initiators are 1,1'-azobis(isobutylonitrile) (AIBN), 1,1'-azobis (cyclohexane-1-carbonitrile), 2,2'-azobis(2-methylbutylonitrile) ,2,2'-azobis(2,4-dimethylvaleronitrile) and 2,2'-azobis(2-methylpropane).

No particular limitation is imposed on the method for carrying out the reaction indicated by formula (V). Generally, an olefin is reacted with trihalogenosilane in the presence of a radical initiator in an autoclave. The reaction is conducted at a temperature of 80–230° C., preferably 100–200° C. for a period of from 30 minutes to 5 days, preferably one hour to 100 hours.

Although the composition of charging the reaction materials is optional, the molar ratio of an olefin to trihalogenosilane is within the range of 1.0 to 0.5, preferably 1.5 to 3.0. The amount of an radical initiator is also optional. In general, the molar ratio of a radical initiator to an olefin is within the range of 0.05 to 1.0.

A first example of the method for synthesizing the inventive alkylsilnae of formula wherein three hydrogen atoms are bonded to the silicone atom, that is, alkyltrihydrosilane is conducted by hydrogenating alkyltrihalogenosilane with use of a metal hydride as indicated by formula (VI)

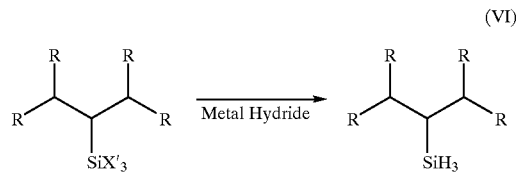

wherein each R is the same as those in formula (Ia) and X' is a halogen atom.

The metal hydride used in this reaction is not restricted but is preferably lithium hydride, sodium hydride, sodium boron hydride and lithium aluminum hydride.

The method for conducting the reaction indicated by formula (VI) may be arbitrary selected. In general, there is employed a method in which the alkyltrihalogenosilane is reacted with the metal hydride in a solvent of a hydrocarbon selected from diethylether, dibutylether and tetrahydrofuran. The reaction should be conducted at a temperature of –20 to 100° C., preferably 0 to 80° C. The reaction time is selective depending on the reaction scale and the reaction vessel but selected from the range of 5 minutes to one day, preferably 10 minutes to 4 hours. Although the amount of the metal hydride is within the range of 0.5 to 4.0, preferably 0.7 to 2.0 by the molar ratio of the metal hydride to alkyltrihalogenosilan.

The intended product may be recovered by deactivating an excess of the metal hydride remaining in the reaction mixture with water or an alcohol and removing the by-product salt by filtration or washing with water, followed by distillation.

A second example of the method for synthesizing the alkyltrihydrosilane is conducted by reacting an olefin with a silane gas (monosilane) in the presence of a radical initiator as indicated by the formula

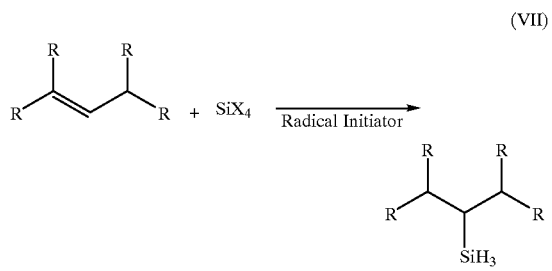
(VII)

wherein each R is the same as those in formula (Ia).

The olefin to be used in the reaction of formula (VII) may be those used for the reaction of formula (V).

Although not restricted, eligible radical initiators are 1,1'-azobis(isobutylonitrile) (AIBN), 1,1'-azobis(cyclohexane-1-carbonitrile), 2,2'-azobis(2-methylbutylonitrile), 2,2'-azobis(2,4-dimethylvaleronitrile) and 2,2'-azobis(2-methylpropane).

Any suitable methods may be employed for conducting the reaction of formula (VII). In general, an olefin is reacted with a silane gas in the presence of a radical initiator in an autoclave. The reaction is conducted at a temperature of 80 to 230° C., preferably 100 to 200° C. for a period of from 30 minutes to 5 days, preferably one hour to 100 hours.

Although the composition of charging the reaction material is optional, the molar ratio of an olefin to trihalogenosilane is within the range of 1.0 to 0.5, preferably 15 to 3.0. The amount of an radical initiator is also optional. In general, the molar ratio of a radical initiator to an olefin is within the range of 0.05 to 1.0.

The intended product can be recovered by distilling the reaction product.

The other inventive silane compound is one represented by the formula

 (I)

wherein Q is a group represented by the formula

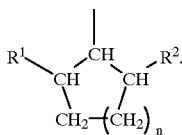
(III)

This silane compound is hereinafter referred to as cycloalkylsilane.

Therefore, the cycloalkylsilane according to the invention is represented by the formula

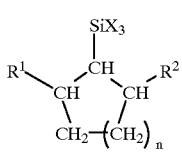
(Ib)

In formula (Ib), X is a hydrogen atom or a halogen atom such as fluorine, chlorine, bromine and iodine among which chlorine is particularly preferred, $R^1$ is a hydrogen atom or a $C_1-C_4$ alkyl group, $R^2$ is a $C_1-C_4$ alkyl group n is an integer of 1 or 2. If $R^1$ is not a hydrogen atom, $R^1$ and $R^2$ may be the same or different.

Specific examples of the alkyl group include methyl, ethyl, n-propyl, n-butyl, iso-propyl, sec-butyl, iso-butyl and tert-butyl groups.

In formula (Ib), $R^1$ is not a hydrogen atom if $R^2$ is a methyl group and n is 2 and if $R^2$ is a methyl group and X is an halogen atom.

Specific examples of cycloalkylsilane represented by formula (Ib) are cycloalkyltrihydrosilane such as 2-methylcyclopentylsilane, 2-ethylcyclopentylsilane, 2-n-propylcyclopentylsilane, 2-n-butylcyclopentylsilane, 2-iso-propylcyclopentylsilane, 2-sec-butylcyclopentylsilane, 2-iso-butylcyclopentylsilane, 2-tert-butylcyclopentylsilane, 2-ethylcyclohexysilane, 2-n-propylcyclohexylsitane, 2-n-butylcyclohexylsilane, 2-iso-propylcyclohexylsilane, 2-sec-butylcyclohexylsilane, 2-iso-butylcyclohexylsilane, 2-tert-butylcyclohexylsilane, 2,5-dimethylcyclopentylsilane, 2,5-diethylcyclopentylsilane, 2,5-di-n-propylcyclopentylsilan, 2,5-di-n-butylcyclopentylsilane, 2,5-di-iso-propylcyclopenthylsilane, 2,5-di-sec-butylcyclopentylsilane, 2,5-d-iso-butylcyclopentylsilane, 2,5-di-tert-butylcyclopentylsilane, 2-ethyl-5-methylcyclopenthylsilane, 2-n-propyl-5-methylcyclopentylsilane, 2-n-butyl-5-methylcyclopentylsilane, 2-n-propyl-5-ethylcyclopentylsilane, 2-n-butyl-5-ethylcyclopentylsilane, 2,6-dimethylcyclohexylsilane, 2,6-diethylcyclohexylsilane, 2,6-di-n-propylcyclohexylsilane, 2,6-di-n-butylcyclohexylsilane , 2,6-di-iso-propylcyclohexylsilane, 2,6-di-sec-butylcyclohexylsilane, 2,6-di-iso-butylcyclohexylsilane, 2,6-di-tert-butyl-cyclohexylsilane, 2-ethyl-6-methylcyclohexylsilane, 2-n-propyl-6-methylcyclohexylsilane, 2-n-butyl-6-methylcyclohexylsilane, 2-n-propyl-6-ethylcyclohexylsilane and 2-n-butyl-6-ethylcyclohexylsilane and cycloalkyltrichlorosilane such as 2-ethylcyclopentyltrichlorosilane, 2-n-propylcyclopentyltrichlorosilane, 2-n-butylcyclopentyltrinclorosilane, 2-iso-propylcyclopentyltrichlorosilane, 2-sec-butyl cyclopentyltrichl orosilane, 2-iso-butylcyclopentyltrichlorosilane, 2-tert-butylcyclopentyltrichlorosilane, 2-ethylcyclohexltrichlorosilane, 2-n-propylcyclohexyltrichlorosilane, 2-n-butylcyclohexyltrichlorosilane, 2-iso-propylcyclohexyltrchlorosilane, 2-sec-butylcyclohexyltrichlorosilane, 2-iso-butylcyclohexyltrichlorosilane, 2-tert-butylcyclohexyltrichlorosilane, 2,5-dimethylcyclopentyltrichlorosilane, 2,5-dimethylcyclopentyltrichlorosilane, 2,5-di-n-propylcyclopentyltrichlorosilane, 2,5-di-n-butylcyclopentyltrichlorosilane, 2,5-di-iso-prpylcyclopentytrichlorosilane, 2,5-di-sec-butylcyclopentyltrichlorosilane, 2,5-di-iso-butylcyclopentyltrichlorosilane, 2,5-di-tert-butylcyclopentyltrichlorosilane, 2-ethyl-5-methylcyclopentyltrichlorosilane, 2-n-propyl-5-methylcyclopentyltrichlorosilane, 2-n-butyl-5-methylcyclopentyltrichlorosilane, 2-n-propyl-5-ethylcyclopentyltrichlorosilan 2-n-butyl-5-ethylcyclopentyltrichlorosilane, 2,6-dimethyleyciohexyltrichiorosilane, 2,6- diethylcyclohexyltrichlorosilane, 2,6-di-n-propylcyclohexylchlorosilane, 2,6-di-n-butylcyclohexyltrichlorosilane, 2,6-di-iso-propylcyclohexyltrichlorosilane, 2,6-di-sec-butylcyclohexyltrichlorosilane, 2,6-di-iso-butylcyclohexyltrichlorosilane, 2,6-di-tert-butylcyclohexyltrichlorosilane, 2-ehtyl-6-methylcyclohexyltrichlorosilane, 2-n-propyl-6-methylcyclohexyltrichlorosilane, 2-n-butyl-6-methylcyclohexyltrichlorosilane, 2-n-propyl-6-ethylcyclohexyltrichlorosilane and 2-n-butyl-6-ethylcyclohexyltrichlorosilane.

In the cycloalkylsilane according to the present invention, two kinds of stereoisomers (cis isomer and trans isomer) are present if $R^1$ in formula (Ib) is a hydrogen atom and three or four kinds of stereoisomers (cis-trans isomer, cis—cis isomer and trans—trans Isomer) are present if $R^1$ in the same is an alkyl group hydrogen atom. Each of these isomers can be easily separated by distillation using a fractionating tower. Upon polymerization of the inventive cycloalkylsilane, it may be subjected to polymerization after the stereoisomers being isolated or as they are.

The cycloalkylsilane according to the invention can be produced by any suitable methods. Although not restricted, typical examples of such a method are as follows.

A first example of synthesizing a cycloalkylsilane of formula (Ib) wherein three halogens are bonded to the silicone atom, that is, cycloalkyltrihalogenosilane is conducted by reacting an organic metal compound represented by the formula

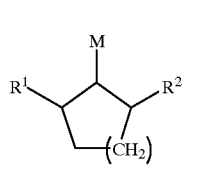

(a')

with tetrahalogenated silicone as indicated by the formula

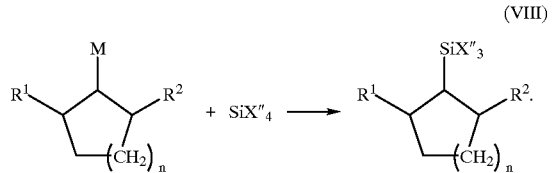

(VIII)

In these formulae, $R^1$ and $R^2$ are these as those in formula (Ib), X" is a halogen atom and M' is lithium or halogenated magnesium.

Specific examples of the organic metal compound of formula (a') are cycloalkyllithium such as 2-methylcyclopentyllithium, 2-ethylcyclopentyllithium, 2-n-propylcyclopentyllithium, 2-n-butylcyclopentyllithium, 2-iso-propylcyclopentyllithium, 2-sec-butylcyclopentyllithium, 2-iso-butylcyclopentyllithium, 2-tert-butylcyclopentyllithium, 2-ethylcyclohexyllithium, 2-n-propylcyclohexyllithium, 2-n-butylcydohexyllithium, 2-iso-propylcyclohexyllithium, 2-sec-butylcyclohexyllithium, 2-iso-butylcyclohexyllithium, 2-tert-butylcyclohexyllithium, 2,5-dimethy, cyclopentyllithium, 2,5-diethylcyclopentyllithium, 2,5-di-n-propylcyclopentyllithium, 2,5-di-nbutylcyclopentyllithium, 2,5-di-iso-propylcyclopentyllithium, 2,5-di-sec-butylcyclopentyllithium, 2,5-di-iso-butylcyclopentyllithium, 2,5-di-tert-butylcyclopentyllithium, 2-ethyl-5-methylcyclopentyllithium, 2-n-propyl-5-methylcyclopentyllithium , 2-n-butyl-5-methylcyclopentyllithium, 2-n-propyl-5-ethylcyclopentyllithium, 2-n-butyl-5-ethylcyclopentyllithium, 2,6-dimethylcyclohexyllithium, 2,6-diethylcyclohenyllithium, 2,6-di-n-propylcyclohexyllithium, 2,6-di-n-butylcyclohexyllithium, 2,6-di-iso-propylcyclohexyllithium, 2,6-di-sec-butylcyclohexyllithium, 2,6-di-iso-butylcydohexyllithium, 2,6-di-tert-butylcyclohexyllithium, 2-ethyl-6-methylcyclohexyllithium, 2-n-propyl-6-methylcyclohexyllithium, 2-n-butyl-6-methylcylohexyllithium, 2-n-propyl-6-ethylcyclohexyllithium and 2-n-butyl-6-ethylcyclohexyllithium and cycloalkylmagnesiumbromide such as 2-methylcyclopentylmagnesiumbromide, 2-ethylcyclopentylmagnesiumbromide, 2-n-propylcyclopentylmagnesiumbromide, 2-n-butylcyclopentylmagnesiumbromide, 2-iso-propylcyclopentylmagnesiumbromide 2-sec-butylcyclopentylmagnesiumbromide, 2-iso-butylcyclopentylmagnesiumbromide, 2-tert-butylcyclopentylmagnesiumbromide, 2-ethylcyclohexylmagnesiumbromide, 2-n-propylcyclohexylmagnesiumbromide, 2-n-butylcyclohexylmagnesiumbromide, 2-iso-propylcyclohexylmagnesiumbromide, 2-sec-butylcyclohexylmagnesiumbromide, 2-iso-butylcyclohexyimagnesiumbromide, 2-tert-butylcyclohexylmagnesiumbromide, 2,5-dimethylcyclopentylmagnesiumbromide, 2,5-dlethylcyclopentylmagnesiumbromide, 2,5-di-n-propylcyclopentylmagnesiumbromide, 2,5-di-n-butylcyclopentylmagnesiumbromide, 2,5-di-iso-propylcyclopentylmagnesiumbromide, 2,5-di-sec-butylcylopentylmagnesiumbromide, 2,5-di-iso-butylcyclopentylmagnesiumbromide, 2,5-di-tert-butylcyclopentylmagnesiumbromide, 2-ethyl-5-methylcyclopentylmagnesiumbromide, 2-n-propyl-5-methylcyclopentylmagnesiumbromide, 2-n-butyl-5-methylcyclopentylmagnesiumbromide. 2-n-propyl-5-ethylcyclopentylmagnesiumbromide, 2-n-butyl-5-ethylcyclopentylmagnesiumbromide, 2,6-dimethylcyclohexylmagnesiumbromide, 2,6-diethylcyclohexylmagnesiumbromide, 2,6-di-n-propylcyclohexylmagnesiumbromide, 2,6-di-n-butylcyclohexylmagnesiumbromide, 2,6-di-iso-propylcyclohexylmagnesiumbromide, 2,6-di-sec-butylcyclohexylmagnesiumbromide, 2,6-di-isobutylcyclohexylmagnesiumbromide, 2,6-di-tert-butylcyclohexylmagnesiumbromide, 2-ethyl-6-methylcyclohexylmagnesiumbromide, 2-n-propyl-6-methylcyclohexylmagunesiumbromide, 2-n-butyl-6-methylcyclohexylmagnesiumbromide, 2-n-propyl-6-ethylcyclohexylmagnesiumbromide and 2-n-butyl-6-ethylcyclohexylmagneiumbromide.

These organic metal compounds can be easily obtained by reacting halogenated cycloalkan with lithium or magnesium in an ethereal solvent such as diethylether and tetrahydrofuran.

The tetrahalogenated silane to be reacted with the organic metal compound may be selected arbitrary but preferred is tetrachlorosilane, There is no particular limitation to the method for conducting the reaction indicated by formula (VIII). In general, the reaction is conducted by adding a solution the organic metal compound of formula (a') in diethylether or tetrahydrofuran to a soutition of the tetrahalogenated silane in ether or the polar solvent of tetrahydrofuran. The reaction temperature is suitably selected depending on the organic metal compound but falls within the range of −20 to 100° C., preferably 0 to 80° C. The reaction is usually carried out for a period of 5 minutes to 10 hours, preferably 20 minutes to 5 hours.

Although the composition of charging the reaction materials is optionally selected, the molar ratio of the organic metal compound to tetrahalogenated silane is to be within the range of usually 0.5 to 1.2, preferably 0.8 to 1.1.

After completion of the reaction, the intended reaction product, that is, cycloalkyltrihalogenosilane can be obtained by filtrating the byproduct salt from the reaction mixture and distilling the filtrate.

A second example of the method for synthesizing the inventive cyclotrihalogenosilane is conducted by reacting a cyclic olefin with trihalogenosilane in the presence of a radical initiator as indicated by formula

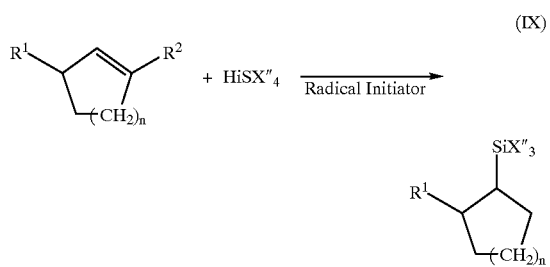

wherein $R^1$ and $R^2$ each are the same as those in formula (Ib) and X" is an halogen atom.

Eligible cyclic olefins for the reaction of formula (IX) are 1-methylcyclopentene, 1-ethylcyclopentene, 1-n-propylcyclopentene, 1-n-butylcyclopentene, 1-iso-propylcyclopentene, 1-sec-butylcyclopentene, 1-iso-butylcydopentene, 1-tert-butylcyclopentene, 1,3-dimethylcyclopentene, 1,3-diethylcydopentene, 1,3-di-n-propylcyclopentene, 1,3-di-n-butylcyclopentene, 1,3-di-iso-propylcydopentene, 1,3-di-sec-butylcyclopentene, 1,3-di-isobutylcyclopentene, 1,3-di-tert-butylcyclopentene, 1-ethyl-3-methylcyclopentene, 1-n-propyl-3-methylcyclopentene, 1-n-butyl-3-methylcyclopentene, 1-n-propyl-3-ethylcyclopentene, 1-n-butyl-3-ethylcyclopentene, 1,3-dimethylcyclohexene, 1,3-diethylcyclohexene, 1,3-di-n-propylcylohexene, 1,3-di-n-butylcylohexene, 1,3-di-iso-propylcyclohexene, 1,3-di-sec-butylcyclohexene, 1,3-di-iso-butylcyclohexene, 1,3-di-tert-butylcydohexene, 1-ethyl-3-methylcyclohexene, 1-n-propyl-3-methylcyclohexene, 1-n-butyl-3-methylcyclohexene, 1-n-propyl-3-ethylcyclohexene and 1-n-butyl-3-ethylcyclohexene.

A variety of trihalogenosilanes are eligible for the reaction with the organic metal compound, among which trichlorosilane is particularly preferred.

Although not restricted, eligible radical initiators are 1,1'-azobis(isobutyronitrile) (AIBN), 1,1-azobis (cyclohexane-1-karbonitrile), 2,2'-azobis(2-methylbutyronitrile), 2,2'-azobis(2,4-dimethylvaleronitrile) and 2,2'-azobis(2-metylpropane).

Although there is no particular limitation to the method for conducting the reaction indicated by formula (IX), it is generally conducted by reacting the cyclic olefin with trihalogenosilane in the presence of the radical initiator in an autogenerative. The reaction temperature is selected from the range of 80 to 230° C., preferably 100 to 200° C. The time required for completing the reaction is selective depending on the reaction scale and the size of a reaction vessel but is usually within the range of 30 minutes to 5 days, preferably 1 hour to 100 hours.

The composition of charging the reaction materials can be determined arbitrary but the molar ratio of the cyclic olefin to the trihalogenosilane is within the range of 1.0 to 5.0, preferably 1.5 to 3.0. Although the amount of the radical initiator is also selective, the molar ratio of the radical initiator to the cyclic olefin is within the range of 0.05 to 1.0.

The intended reaction product can be easily recovered by distilling the reaction mixture.

A first example of synthesizing the inventive cycloalkylsilane represented by formula (Ib) wherein three hydrogen atoms are bonded to the silicone atom, that is, cycloalkyl-trlhydrosilane is conducted by hydrogenating cycloalkyltrihalogenosilane using a metal hydride as indicated by the formula

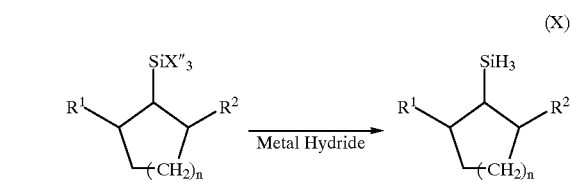

wherein $R^1$ and $R^2$ each are the same as those in formula (Ib) and X" is a halogen atom.

Eligible metal hydrides for this reaction are lithium hydride, sodium hydride, sodium borohydride and lithium aluminum hydride.

Although there is no particular limitation imposed upon the method for conducting the reaction of formula (X), there is generally employed a method in which alkyltrihalogenosilane is reacted with the metal hydride in an ethereal solvent such as diethylether, dibutylether and tetrahydrofuran or in a hydrocarbonous solvent such as benzenetoluene and hexane. The reaction temperature is within the range of usually −20 to 100° C., preferably 0 to 80° C. The time required for completing the reaction is selected depending on the reaction scale and the size of a reaction vessel but is within the range of usually 5 minutes to one day, preferably 10 minutes to 4 hours.

Although there is no particular limitation imposed on the amount of the metal hydride, the molar ratio of the metal hydride to alkyltrihalogenosilane is within the range of 0.5 to 4.0, preferably 0.7 to 2.0.

The intended reaction product can be recovered by deactivating the metal hydride remaining in the reaction mixture with use of water or an alcohol and distilling after the byproduct salt being removed by filtration or water-washing.

A second example of the method for synthesizing the inventive cycloalkyltrihydrosilane is conducted by reacting a cyclic olefin with silane (monosilane) in the presence of a radical initiator so as to hydrosilate the cyclic olefin as indicated by formula

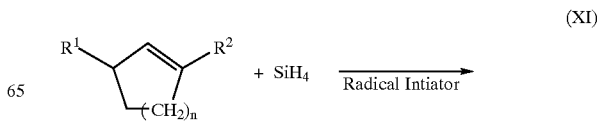

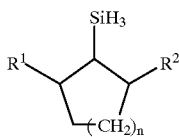

wherein $R^1$ and $R^2$ each are the same as those in formula (Ib).

Eligible cyclic olefins and radical initiators for the reaction of formula (XI) are those used for the reaction of formula (IX).

Although there is no particular limitation imposed upon the method for conducting the reaction of formula (IX), there is generally employed a method in which the cyclic olefin is reacted with gaseous silane in an autoclave. The reaction temperature is selected from the range of usually 80 to 230° C., preferably 100 to 200° C. The time required for completing the reaction is selected depending on the reaction scale and the size of the reaction vessel but is on the order of usually 30 minutes to 5 days, preferably one hour to 100 hours.

The molar ratio of the cyclic olefin to a gaseous silane is selected arbitrary but is within the rage of usually 1.0 to 5.0, preferably 1.5 to 3.0.

Although the amount of the radical initiator is also selective, the molar ratio of the radical initiator to the cyclic olefin is within the range of 0.05 to 1.0.

The intended reaction product can easily be obtained by distilling the reaction mixture.

The inventive silane compounds represented by formulae (Ia) and (Ib) are useful monomers for the production of polysilanes which can be utilized as the precursors of electroconductive- and photoconductive-materials and phtoreactive materials such as photoresist as well as polymerization initiators and silicone carbide-based ceramics. Furthermore, the inventive silane compounds are also useful for chemical decomposition. Polysilanes derived from the inventive silane compounds are those having network-like molecular structures and are advantageous in that the hydrocarbon substituents are excellent in elimination properties.

EXAMPLES

The following examples are presented to illustrate specific embodiments of the present invention and should not be interpreted as limitations upon the scope of the invention.

Example 1
2,4-dimethyl-3-trichlorosilylpentane

A one-liter autoclave equipped with a stirrer was charged in a nitrogen atmosphere with 55 grams (0.56 mol) of 2,4-dimethyl-3-pentene, 148 grams (1.1 mol) of trichlorosilane and 17 grams (70 mmols) of 1,1'-azobis(cyclohexane-1-carbonitrile) and the mixture was reacted at a temperature of 130° C. for 4 days. The resulting reaction mixture was purified by distillation thereby obtaining 117 grams (0.50 mol) of 2,4-dimethyl-3-trichlorosilylpentane. The structure of the resulting product was identified by $^1$HNMR.

Yield: 89% Boiling point: 110–120° C./80 mmHg; $^1$HNMR Spectrum (in CDCl3); 2.29 (m, 2H, $\equiv$CH, J=4.0, J=7.0); 1.38 (t, 1H, $=$CHSi, J=4.0); 1.17, 1.14 (d×2, 12H, —CH3, J=7.0); Mass Spectrum $C_7H_{15}SiCl_3$ Calc'd: C 35.99, H 6.47, Si 12.02, Cl 45.52; Found: C 36.22, H 6.41, Si 12.17, Cl 45.20.

Example 2
2,4-dimethyl-3-silylpentane

A one-liter four-necked flask equipped with a stirrer, a reflux cooling tube and a dropping funnel was charged with 50 grams (1.3 mol) of lithium aluminum hydride and one liter of diethylether under a nitrogen atmosphere. The mixture was added with droplets of a mixture of 117 grams (0.50 mol) of 2,4dimethyl-3-trichlorosilylpentane obtained in Example 1 and 200 ml of diethylether over 2 hours with stirring. After completion of the dropwise addition, the mixture was reacted on heating under reflux for 2 hours.

After completion of the reaction, the resulting mixture was added with droplets of 40 ml of water as being cooled with ice and then added with one liter of diluted hydrochloric acid and 500 ml of diethylether in turn, followed by three times-washing with 500 ml water after separating the organic phase. Thereafter, the organic phase was dehydrated with anhydrous magnesium sulfate and filtered out. The filtrate was purified by distillation thereby obtaining 39 grams (0.30 mol) of 2,4-dimethyl-3-silylpentane. The identification of the structure of the resulting product was conducted by $^1$H-NMR.

Yield: 60% Boiling Point: 125–1228° C./; $^1$H-NMR Spectrum (in CDCl3); 3.44 (d, 3H, —SiH$_3$, J=4.0); 1.91 (oxtet, 2H, $\equiv$CH, J=6.6); 0.97, 0.95 (d×2, 12H, —CH$_3$, J=6.6); Mass Spectrum $C_7H_{19}Si$ Calc'd: C 64.52, H 13.92, Si 21.55; Found: C 64.81, H 13.75, Si 21.44;

Example 3
3,5-diethyl-4-trichlorosilylheptane

A one-liter autoclave equipped with a stirrer was charged in a nitrogen atmosphere with 77 grams (0.50 mol) of 3,5-diethyl-3-heptene, 134 grams (1.0 mol) of trichlorosilane and 24 grams (0.1mol) of 1,1'-azobis(cyclohexane-1-carbonitrile) and the mixture was reacted at a temperature of 130° C. for 5 days. The resulting reaction mixture was purified by distillation thereby obtaining 80 grams (0.28 mol) of 3,5-diethyl-4-trichlorosilylheptane. The structure of the resulting product was identified by $^1$H-NMR.

Yield: 55% Boiling point: 130–135° C./10 mmHg; $^1$H-NMR Spectrum (in CDCl$_3$); 2.21–2.39 (m, 2H, $\equiv$CH); 1.65–1.83 (m, 8H, $=$CH$_2$); 1.38 (t, 1H, $=$CHSi, J=4.1); 1.14, 1.07 (t×2, 12H, —CH$_3$, J=6.8); Mass Spectrum $C_{11}H_{23}SiCl_3$ Calc'd: C 45.60, H 8.00, Si 9.69, Cl 36.71; Found: C 45.29, H 8.13, Si 9.85, Cl 36.73;

Example 4
3,5-diethyl-4-silylheptane

A one-liter four-necked flask equipped with a stirrer, a reflux cooling tube and a dropping funnel was charged with 27 grams (0.71 mol) of lithium aluminum hydride and 500 ml of diethylether under a nitrogen atmosphere. The mixture was added with droplets of a mixture of 80 grams (0.28 mol) of 3,5-diethyl-4-trichlorosilylheptane obtained in Example 3 and 100 ml of diethylether over 2 hours. After completion of the dropwise addition, the mixture was reacted on heating under reflux for 2 hours with stirring.

After completion of the reaction, the resulting mixture was added with droplets of 30 ml of water as being cooled with ice and then added with 500 ml of diluted hydrochloric acid and 500 ml of diethylether in turn, followed by three times-washing with 500 ml water after separating the organic phase, Thereafter, the organic phase was dehydrated with anhydrous magnesium sulfate and filtered out. The filtrate was purified by distillation thereby obtaining 28 grams (0.12 mol) of 3,5-diethyl-4-silylpentane. The identification of the structure of the resulting product was conducted by $^1$H-NMR.

Yield: 43% Boiling Point: 92–98° C./20 mmHg; $^1$H-NMR Spectrum (in CDCl3); 3.46 (d, 3H, —SiH3, J=4.0); 2.02 (m, 2H, ≡CH); 1.55–1.80 (m, 8H, =CH2); 1.02, 0.97 (t×2, 12H, —CH3, J=6.8); 0.71–0.82 (m, 11H, =CHSi); Mass Spectrum $C_{12}H_{28}Si$ Calc'd: C 71.91, H 14.08, Si 14.01; Found: C 71.58, H 14.10, Si 14.32.

Example 5
3,5-dimethyl-4-trichlorosilylheptane

A one-liter autoclave equipped with a stirrer was charged in a nitrogen atmosphere with 76 grams (0.60 mol) of 3,5-dimethyl-3-heptene, 161 grams (1.2 mol) of trichlorosilane and 29 grams (0.12 mol) of 1,1'-azobis(cyclohexane-1-carbonitrile) and the mixture was reacted at a temperature of 130° C. for 5 days. The resulting reaction mixture was purified by distillation thereby obtaining 92 grams (0.35 mol) of 3,5-dimethyl-4-trichlorosilylheptane. The structure of the resulting product was identified by $^1$H-NMR.

Yield: 58% Boiling Point: 100–110° C./40 mmHg; $^1$H-NMR Spectrum (in CDCl3); 2.21–2.39 (m, 2H, ≡CH); 1.55–1.76 (m, 8H, =CH$_2$); 1.43 (t, 1H, =CHSi, J =4.1); 1.08 (d, 6H, —CH$_3$, J=6.8); 1.05 (t, 6H, —CH$_3$, J=6.8); Mass Spectrum $C_9H_{19}SiCl_3$ Calc'd: C 41.31, H 7.32, Si 10.73, Cl 40.64; Found: C 41.86, H 7.78, Si 10.21, Cl 40.15.

Example 6
3,5-dimethyl-4-silylheptane

A one-liter four-necked flask equipped with a stirrer, a reflux cooling tube and a dropping funnel was charged with 33 grams (0.83 mol) of lithium aluminum hydride and 500 ml of diethylether under a nitrogen atmosphere. The mixture was added with droplets of a mixture of 92 grams (0.35 mol) of 3,5-dimethyl-4-trichlorosilylpentane obtained in Example 5 and 100 ml of diethylether over 2 hours with stirring. After completion of the dropwise addition, the mixture was reacted on heating under reflux for 2 hours.

After completion of the reaction, the resulting mixture was added with droplets of 40 ml of water as being cooled with ice and then added with 500 ml of diluted hydrochloric acid and 500 ml of diethylether in turn, followed by three times-washing with 500 ml water after separating the organic phase. Thereafter, the organic phase was dehydrated with anhydrous magnesium sulfate and filtered out. The filtrate was purified by distillation thereby obtaining 22 grams (0.12 mol) of 3,5-dimethyl4-silylpentane. The identification of the structure of the resulting product was conducted by 1H-NMR.

Yield: 40% Boiling Point: 90–95° C./100 mmHg; $^1$H-NMR Spectrum (in CDCl3); 3.44 (d, 3H, —SiH$_3$, J=4.0); 1.93 (m, 2H, ≡CH); 1.70–1.82 (m, 8H, =CH$_2$); 1.01 (d, 6H, —CH$_3$, J=6.6); 0.95 (t, 6H, —CH$_3$, J=6.7); 0.77–0.83 (m, 1 H, =CHSi); Mass Spectrum $C_9H_{22}Si$ Calc'd: C 68.26, H 14.00, Si 17.74; Found: C 68.55, H 13.82, Si 17.63.

Example 7
2-methylcyclopentylsilane

A one-liter autoclave equipped with a stirrer was charged in a nitrogen atmosphere with 65 grams (0.79 mol) of 1-methylcyclopentene, 242 grams (1.79 mol) of trichlorosilane and 29 grams (0.12 mol) of 1,1'-azobis(cydohexane-1-carbonitrile) and the mixture was reacted at a temperature of 120° C. for 3 days. The resulting reaction mixture was purified by distillation thereby obtaining 148 grams of 3,5-dimethyl-4-trichlorosilylheptane.

Thereafter, a one-liter four-necked flask equipped with a stirrer, a reflux cooling tube and a dropping funnel was charged with 60 grams (1.6 mol) of lithium aluminum hydride and one liter of diethylether under a nitrogen atmosphere. The mixture was added with droplets of a mixture of 148 grams (0.68 mol) of 2-methylcyclopentyltrichlorosilane and 80 ml of diethylether over 3 hours with stirring. After completion of the dropwise addition, the mixture was reacted on heating under reflux for 2 hours.

After completion of the reaction, the resulting mixture was added with droplets of 80 ml of water as being cooled with ice and then added with 500 ml of diluted hydrochloric acid and 500 ml of diethylether in turn, followed by three times-washing with 500 ml water after separating the organic phase. Thereafter, the organic phase was dehydrated with anhydrous magnesium sulfate and filtered out. The filtrate was purified by distillation thereby obtaining 28 grams of cis-2-methylcyclopentylsilane represented by the formula

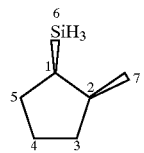

and 16 grams of trans-2-methylcyclopentylsilane represented by the formula

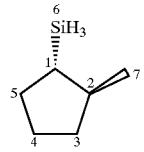

Each of the resulting product was identified in structure by $^1$H-NMR. cis-2-methylcyclopentsilane Boiling Point: 115–116° C. (atmospheric pressure); $^1$H-NMR Spectrum (in CDCl3); (the assignment was identified by two-dimensional NMR Spectrum); H-1 : 1.34–1.40 (m, 1H); H-2 : 2.25 (m, 1H); H-3, H-5: 1.69–1.78 (m, 2H); H-3': 1.25–1.32 (m 1H); H-4: 1.86–1.92(m, 1H); H-4', H-5': 1.50–1.59 (m, 2H); H-6: 3.48 (d, 3H, $J_{1.5}$=4.0); H-7: 0.96 (d, 3H, $J_{2.7}$=6.0 Hz); Mass Spectrum $C_6H_{14}Si$ (cis form) Calc'd : C 63.07, H 12.35, Si 24.58; Found: C 62.81, H 12.48, Si 24.71.
trans-2-methylcyclopentylsilane Boiling Point: 105–108° C.; $^1$H-NMR Spectrum (in CDCl3); (the assignment was identified by NMR Spectrum) H-1: 0.65–0.76 (m, 1H); H-2: 1.68–1.74 (m, 1H); H-3: 1.81–1.87 (m, 1H); H-3': 1.11–1.17 (m, 1H); H-4; H-4': 1.55–1.67 (m, 2H); H-5: 1.91–1.97 (m, 1H); H-5': 1.41–1.48 (m, 1H); H-6: 3.50 (d, 3H, $J_{1.5}$=4.0); H-7: 1.04 (d, 3H. $J_{2.7}$=6.0); Mass Spectrum $C_6H_{14}Si$ (trans form) Calc'd: C 63.07, H 12.35, Si 24.58; Found: C 62.74, H 12.56, Si 24.70.

Example 8
2,6-dimethylcyclohexyltrichlorosilane

A one-liter autoclave equipped with a stirrer was charged in a nitrogen atmosphere with 39 grams (0.35 mol) of 1,3-dimethylcyclohexene, 94 grams (0.69 mol) of trichlorosilane and 18 grams (74 mmol) of 1,1'-azobis (cydohexane-1-carbonitrile) and the mixture was reacted at a temperature of 130° C. for 3 days. The resulting reaction mixture was purified by distillation thereby obtaining 69 grams (0.28 mol) of 2,6-dimethyl-4-cyciohexyltrichlorosilane, The structure of the resulting product was Identified by $^1$H-NMR analysis.

Yield: 80% Boiling Point: 130–135° C./80 mmHg; $^1$H-NMR Spectrum (in CDCl3); 2.28–2.50; 1.15–2.03 (m, 9H); 1.13 (d, 3H, J=7.0, —CH3); 1.09 (d, 3H, J=7.0, —CH3); Mass Spectrum $C_8H_{15}SiCl_3$ Calc'd: C 39.12, H 6.15, Si 11.43, Cl 43.30; Found: C 38.96, H 6.24, Si 11.18, Cl 43.62.

Example 9
2,6-dimethylcyclohaxylsilane

A one-liter four-necked flask equipped with a stirrer, a reflux cooling tube and a dropping funnel was charged with 25 grams (0.66 mol) of lithium aluminum hydride and 500 ml of diethylether under a nitrogen atmosphere. The mixture was added with droplets of a mixture of 69 grams (0.28 mol) of 2,6-dimethylcydohexyltrichlorosilane obtained in Example 8 and 100 ml of diethylether over 2 hours with stirring. After completion of the dropwise addition, the mixture was reacted on heating under reflux for 2 hours.

After completion of the reaction, the resulting mixture was added with droplets of 40 ml of water as being cooled with ice and then added with 300 ml of diluted hydrochloric acid and 300 ml of diethylether in turn, followed by three times-washing with 500 ml water after separating the organic phase. Thereafter, the organic phase was dehydrated with anhydrous magnesium sulfate and filtered out. The filtrate was purified by distillation thereby obtaining 34 grams (0.24 mol) of 2,6-dimethylcyclohexylsilane in which three types of isomers are present. The identification of the structure of the resulting product was conducted by 1H-NMR.

Yield: 85% Boiling Point: 88–98° C./100 mmHg; $^1$H-NMR Spectrum (in CDCl3); (The assignment was identified by two-dimensional NMR Spectrum.) 3.52, 3.46, 3.42 (d×3, —SiH$_3$, $J_{1,7}$=4.0, ratio 0.07/1.0/0.2); 1.95–2.08 (m, 1H); 1.63–1.77 (m, 3H); 1.40–1.60 (m, 5H); 0.90–1.03 (m, 6H, —CH$_3$); Mass Spectrum $C_8H_{18}Si$ Calc'd: C 67.52, H 12.75, Si 19.73; Found: C 67.28, H 12.91, Si 19.81.

Furthermore, the 2,6-dimethylcyclohexylsilane thus obtained was purified with use of a fractionating tower thereby obtaining 10 grams (70 mmol) of cis-trans-2,6-dimethylcyclohexylsilane represented by the formula

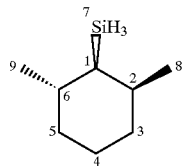

Boiling Point: 94–96° C./100 mmHg; $^1$H-NMR Spectrum (in CDCl3); (The assignment was identified by two-dimensional NMR Spectrum.); H-1,5: 1.00 (m, 2H, $J_{1,6}$=9.0, $J_{1,2}$=4.2); H-2: 2.03(m,1H); H-3,3': 1.46 (m, 2H); H-4: 155 (m, 1H); H-4': 1.50 (m, 1H); H-5': 1.67 (m, 1H); H-6: 1.72 (m, 1H); H-7: 3.47 (d, 3H, $J_{1,7}$=3.0); H-8: 0.98 (d, 3H, $J_{2,8}$=7.2); H-9: 0.93 (d, 3H, $J_{6,9}$=6.6).

Example 10
2,5-dimethylcyclopentyltrichlorosilane

A one-liter autoclave equipped with a stirrer was charged in a nitrogen atmosphere with 49 grams (0.51 mol) of 1,3-dimethylcyclopentene, 138 grams (1.0 mol) of trichlorosilane and 24 grams (0.1 mol) of 1,1'-azobis(cyclohexane-1-carbonitrile) and the mixture was reacted at a temperature of 130° C. for 3 days. The resulting reaction mixture was purified by distillation thereby obtaining 85 grams (0.37 mol) of 2,5-dimethylcyclopentyltrichlorosilane. The structure of the resulting product was identified by $^1$H-NMR analysis.

Yield: 73% Boiling Point: 120–125° C./85 mmHg; $^1$H-NMR Spectrum (in CDCl3); 2.12–2.42; 1.11–2.09 (m, 7H); 1.08 (d, 3H, J=7.0 Hz, —CH$_3$); 1.05 (d, 3H, J=7.0 Hz, —CH$_3$); Mass Spectrum $C_7H_{13}SiCl_3$ Calc'd: C 36.30, H 5.66, Si 12.13, Cl 45.92; Found: C 35.90, H 5.38, Si 12.44, Cl 46.28.

Example 11
2,5-dimethylcyclopentylsilane

A one-liter four-necked flask equipped with a stirrer, a reflux cooling tube and a dropping funnel was charged with 35 grams (0.92 mol) of lithium aluminum hydride and 500 ml of diethylether under a nitrogen atmosphere. The mixture was added with droplets of a mixture of 85 grams (0.37 mol) of 2,5-dimethylcydopentyltrlchlorosilane obtained in Example 10 and 100 ml of diethylether over 2 hours with stirring. After completion of the dropwise addition, the mixture was reacted on heating under reflux for 2 hours.

After completion of the reaction, the resulting mixture was added with droplets of 50 ml of water as being cooled with ice and then added with 300 ml of diluted hydrochloric acid and 300 ml of diethylether in turn, followed by three times-washing with 500 ml water after separating the organic phase. Thereafter, the organic phase was dehydrated with anhydrous magnesium sulfate and filtered out. The filtrate was purified by by distillation thereby obtaining 28 grams (0.22 mol) of 2,5-dimethylcyclopentylsilane. The identification of the structure of the resulting product was conducted by 1H-NMR.

Yield: 59% Boiling Point: 80–92° C./100 mmHg; $^1$H-NMR Spectrum (in CDCl3); (The assignment was identified by two-dimensional NMR Spectrum.); 3.53, 3.48, 3.43 (d×3, —SiH$_3$, 0.13/1.0/0.3); 2.02–2.23 (m, 1H); 1.60–1.80 (m, 2H); 1.25–1.57 (m, 4H); 0.90–1.10 (m, 6H, —CH$_3$); Mass Spectrum $C_7H_{16}Si$ Calc'd: C 65.54, H 12.57, Si 21.89; Found: C 65,27, H 12.69, Si 22.04.

Example 12
2-tert-butylcyclopentyltrichlorosilane

A one-liter autoclave equipped with a stirrer was charged in a nitrogen atmosphere with 50 grams (0.40 mol) of 1-tert-butylcyclopentene, 108 grams (0.80 mol) of trichlorosilane and 20 grams (82 mmol) of 1,1'-azobis (cyclohexane-1-carbonitrle) and the mixture was reacted at a temperature of 130° C. for 3 days. The resulting reaction mixture was purified by distillation thereby obtaining 62 grams (0.24 mol) of 2-tert-butylcyclopentyltrichlorosilane. The structure of the resulting product was identified by $^1$H-NMR.

Yield: 60% Boiling Point: 150–160° C./20 mmHg; $^1$H-NMR Spectrum (in CDCl3); 2.25–2.40 (m, 1H); 1.20–2.10 (m, 7H); 1.12, 1.05 (s, 9H, CH$_3$); Mass Spectrum $C_9H_{17}SiCl_3$ Calc'd : C 41.63, H 6.60, Si 10.82, Cl 40.96; Found: C 41.14, H 6.38, Si 10.96, Cl 41.52.

Example 13
2-tert-butylcyclopentylsilane

A one-liter four-necked flask equipped with a stirrer, a reflux cooling tube and a dropping funnel was charged with 23 grams (0.61 mol) of lithium aluminum hydride and 400 ml of diethylether under a nitrogen atmosphere. The mixture was added with droplets of a mixture of 62 grams (0.24 mol) of 2-tert-butylcyclopentyltrichlorosilane obtained in Example 10 and 50 ml of diethylether over one hour with stirring- After completion of the dropwise addition, the mixture was reacted on heating under reflux for 2 hours.

After completion of the reaction, the resulting mixture was added with droplets of 30 ml of water as being cooled with ice and then added with 200 ml of diluted hydrochloric acid and 300 ml of diethylether in turn, followed by three times-washing with 500 ml water after separating the organic phase. Thereafter, the organic phase was dehydrated with anhydrous magnesium sulfate and filtered out, followed by purification by distillation thereby obtaining 32 grams (0.20 mol) of 2-tert-butylcyclopentylsilane in which two types of isomers are present. The identification of the structure of the resulting product was conducted by 1H-NMR.

Yield: 85% Boiling Point: 100–110° C./80 mmHg; $^1$H-NMR Spectrum (in CDCl3); (The assignment was identified by two-dimensional NMR Spectrum.); 3.47, 3.54 (d×3, —SiH$_3$, J=3,9); 1.73–1.87 (m, 1H, H–2); 1.50–1.75, 1.17–1.42, 0.71–0,80 (m, 7H); 1.05, 0.97 (s, 9H); Mass Spectrum C$_9$H$_{20}$Si Calc'd: C 69.14, H 12.89, Si 17.96; Found: C 68.86, H 12.93, Si 18.21.

What is claimed is:

1. A silane compound represented by the formula

   (I)

wherein X is a hydrogen atom or a halogen atom, Q is selected from a group represented by the formula

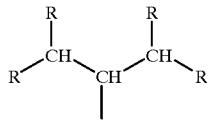   (II)

wherein R is a methyl or ethyl group and may be the same or different, and a group represented by the formula

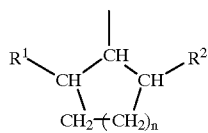   (III)

wherein $R^1$ is a hydrogen atom or a C$_1$–C$_4$ alkyl group, $R^2$ is a C$_1$–C$_4$ alkyl group and n is an integer of 1 or 2, provided that $R^1$ is not an hydrogen atom if $R^2$ is a methyl group and n is 2 or $R^2$ is a methyl group and X in formula (I) is a halogen atom.

2. A silane compound according to claim 1 which is useful for the production of a polysilane and for chemical vapor deposition.

3. A silane compound according to claim 1 wherein said halogen atom is selected from the group consisting of fluorine, chlorine, bromine and iodine.

4. A silane compound according to claim 1 wherein $R^1$ and $R^2$ in said formula (II) each are selected from the group consisting of methyl, ethyl, n-propyl, n-butyl, isopropyl, sec-butyl, Iso-butyl and tert-butyl groups.

* * * * *